(12) United States Patent
De Clerck

(10) Patent No.: US 7,632,097 B2
(45) Date of Patent: Dec. 15, 2009

(54) METHOD FOR MANUFACTURING A SUPRASTRUCTURE AND A CORRESPONDING DRILL JIG

(75) Inventor: René De Clerck, Tervuren (BE)

(73) Assignee: Dental Vision B.V.B., Tervuren (BE)

( * ) Notice: Subject to any disclaimer, the term of this patent is extended or adjusted under 35 U.S.C. 154(b) by 277 days.

(21) Appl. No.: 10/482,927

(22) PCT Filed: Jul. 8, 2002

(86) PCT No.: PCT/BE02/00117

§ 371 (c)(1),
(2), (4) Date: Aug. 23, 2004

(87) PCT Pub. No.: WO03/003933

PCT Pub. Date: Jan. 16, 2003

(65) Prior Publication Data

US 2005/0112524 A1    May 26, 2005

(30) Foreign Application Priority Data

Jul. 6, 2001    (BE) .................................. 2001/0463

(51) Int. Cl.
*A61C 13/225* (2006.01)
*A61C 8/00* (2006.01)

(52) U.S. Cl. .......................... 433/215; 433/76; 433/173

(58) Field of Classification Search ............... 433/76, 433/75, 172, 173, 215
See application file for complete search history.

(56) References Cited

U.S. PATENT DOCUMENTS

| 5,320,529 | A   | 6/1994  | Pompa |
| 5,484,285 | A   | 1/1996  | Morgan |
| 5,630,717 | A * | 5/1997  | Zuest et al. ................. 433/172 |
| 5,725,376 | A * | 3/1998  | Poirier ...................... 433/172 |
| 5,967,777 | A * | 10/1999 | Klein et al. ................... 433/75 |
| 6,224,373 | B1* | 5/2001  | Lee et al. .................... 433/172 |
| 6,319,000 | B1  | 11/2001 | Branemark |

FOREIGN PATENT DOCUMENTS

EP    0 534 552    3/1993

* cited by examiner

*Primary Examiner*—Cris L Rodriguez
*Assistant Examiner*—Michael R Ballinger
(74) *Attorney, Agent, or Firm*—Browdy & Neimark, PLLC

(57) ABSTRACT

The invention concerns a method for manufacturing a suprastructure (7) with artificial teeth (8) which is mounted on at least one implant (9,10) that is provided in the cavity of the mouth of a person and that has to be fixed to the bone of the lower jaw or the upper jaw (1), whereby a drill jig (3) is manufactured with at least one opening (4) for performing a boring (5) in the bone for mounting said implant (9,10), with the feature that the position of said opening (4) in the drill jig (3) and the position of the latter is determined in relation to at least one reference organ (2) that is fixed to said bone.

17 Claims, 1 Drawing Sheet

METHOD FOR MANUFACTURING A SUPRASTRUCTURE AND A CORRESPONDING DRILL JIG

BACKGROUND OF THE INVENTION

1. Technical Field of the Invention

The invention relates to a method for producing a superstructure provided with artificial teeth, which superstructure is fitted on at least one implant, which is provided in the oral cavity of a person and has to be fixed in the bone of a lower or an upper jaw, an aligning plate with at least one aperture being produced for the purpose of drilling a hole in the bone through said aperture, in order to fit the abovementioned implant.

2. Prior Art

The method used according to the prior art for producing such a superstructure is very laborious and protracted for a patient. In a first step, a wax model of a dental prosthesis is made using an impression that is taken of the patient's jaw. A replica of this wax model is then prepared in synthetic resin, in which replica openings are already provided, corresponding to a possible position for the implants, for the purpose of drilling holes in the jaw. A so-called CT scan then has to be made of this replica when it has been placed on the corresponding jaw of the patient, in order to determine the anatomical bone structure and the precise location of nerve bundles and blood vessels. In this way it is checked whether the drilling of holes for the implants is possible, taking into account the anatomical structure of the jaw, such as, inter alia, the position of nerve bundles or blood vessels present there. If it is found that the proposed position of the implants is unsuitable because, for example, nerve bundles or blood vessels would be touched during the drilling of holes, a new or an adapted model has to be produced.

In a subsequent step, an aligning plate is then produced on the basis of the abovementioned replica, and the implants are placed in position. When these implants have been placed and the gums and the bone have healed after this surgical procedure, a number of impressions of the jaw together with the implants are taken, in order to produce a provisional model, i.e. a wax model, of the superstructure. This provisional model then has to be fitted on the patient If the provisional model is satisfactory, the final superstructure is produced on the basis of this provisional model.

In a variant of the above method, the abovementioned first step is to make a CT scan of the jaw on which the superstructure is to be fixed, and an aligning plate is produced directly, on the basis of the electronic information from this CT scan. The superstructure is then further produced according to the technique described above.

Owing to the different steps required in the case of these processes, a patient generally undergoes six months of treatment before a final superstructure is fitted.

Another method according to the prior art makes use of prefabricated superstructures. However, a disadvantage of this method is that for fitting of the superstructure part of the bone of the upper jaw or of the lower jaw has to be removed Furthermore, the prostheses placed in this way are not adapted to the individual shape of a person's jaw.

OBJECT AND SUMMARY OF THE INVENTION

The object of the invention is to overcome the abovementioned disadvantages by proposing a method that allows holes that are necessary for the placing of implants to be drilled in a very simple and accurate manner. This method has the further advantage that the production of a superstructure and its fitting on a person's jaw can be performed in a very short time.

To this end, at least one reference element is fixed to the abovementioned bone, and the location of anatomical structures of the abovementioned jaw relative to this reference element is then determined, means being provided on the abovementioned aligning plate for fixing the latter on the abovementioned jaw relative to the abovementioned reference element and, taking into account the determined location of the anatomical structures, the position of the abovementioned aperture in the aligning plate is determined in such a way that critical anatomical structures, such as nerve bundles or blood vessels, are not touched during the drilling of the abovementioned hole when the aligning plate has been fixed on the abovementioned jaw.

A screw is expediently fixed in the abovementioned bone, said screw forming the abovementioned reference element According to a special embodiment of the method according to the invention, means are provided on the abovementioned aligning plate for fixing the latter detachably on the abovementioned reference element before the abovementioned hole is drilled in the bone. More particularly, the abovementioned means are formed by providing an opening in the aligning plate, which opening connects up in a virtually exact fit with the abovementioned reference element.

According to a preferred embodiment of the method according to the invention, a dental impression is made of the abovementioned jaw with the abovementioned reference element, and a provisional model of the abovementioned superstructure with teeth is made on the basis of this impression, a three-dimensional image being made of the abovementioned jaw together with this provisional model and the abovementioned reference element In an advantageous manner, the abovementioned aligning plate is made on the basis of the abovementioned three-dimensional image.

The abovementioned three-dimensional image is preferably processed electronically in order to produce the abovementioned aligning plate and/or the abovementioned superstructure by means of a so-called rapid prototyping technique.

According to an advantageous embodiment of the method according to the invention, the abovementioned aligning plate is fixed to the abovementioned reference element, and the abovementioned hole is drilled in the jaw, and the implant is fixed in said hole, and subsequently, preferably after the abovementioned reference element has been removed, the abovementioned superstructure is fitted on said implant.

The invention also relates to an aligning plate for use of the method, having at least one aperture for drilling a hole in the bone of a lower or an upper jaw of a person, in order to place at least one implant. Said aligning plate is characterized in that it has means for fixing it to at least one reference element that is provided in the abovementioned bone.

Said means preferably have an opening that connects up in a virtually exact fit with the abovementioned reference element, so that the aligning plate can be fixed detachably on the reference element by means of at least one screw or bolt.

BRIEF DESCRIPTION OF THE DRAWING

Other details and advantages of the invention will emerge from the description that follows of a number of embodiments of the method and the aligning plate according to the invention; this description is given merely as an example and does not limit the scope of the protection claimed; the reference numerals used below relate to the appended figures.

In the various figures the same reference numerals relate to the same or similar elements.

DETAILED DESCRIPTION OF THE PREFERRED EMBODIMENT (S) OF THE INVENTION

The invention relates in general to a method for producing a dental prosthesis which has to be fixed upon so-called, implants provided in the jawbone of a patient. Such a dental prosthesis comprises a so-called superstructure, on which artificial teeth are provided, in a manner that is known per se, and which has fixing means for fixing to the abovementioned implants. Apart from that, the invention also relates to a method for producing an aligning plate that makes it possible in a simple manner to drill very accurate holes, in which said implants are placed.

Figure 1:
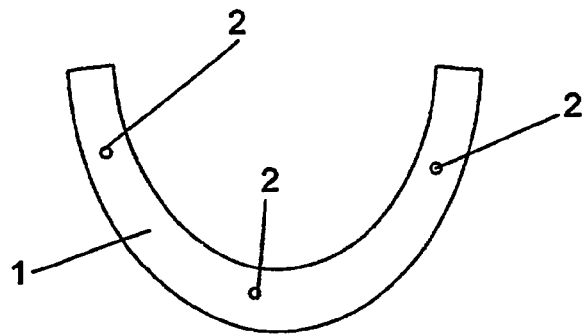
FIG. 1 is a diagrammatic top view of a part of a lower jaw with reference elements according to the invention.

In the case of the method according to the invention, reference elements are fixed in the jaw on which the superstructure is to be placed. FIG. 1 shows diagrammatically a toothless lower jaw 1 in the case of which three reference elements have been fixed in the bone of said jaw. Each of these reference elements is formed by a screw 2.

Said screws 2 are fixed in different positions in the bone of the jaw 1, in such a way that they project slightly above the gum surrounding the bone. Furthermore, the screws 2 are relatively short; but they are still sufficiently long, for example almost 5 mm, to be anchored stably in the jaw.

A dental impression of said jaw 1, together with the screws 2, is then made in the known manner. On the basis of this impression, a so-called bite plate is produced, which allows the position of the upper jaw of the patient to be determined relative to that of the lower jaw.

Owing to the fact that when the abovementioned impression is being taken, the abovementioned screws 2 extend above the gums, during the production of the bite plate corresponding hollows are formed in the underside of the bite plate, which hollows permit said bite plate to be positioned in an exact position in the oral cavity, the abovementioned hollows connecting up in a virtually exact fit with the screws 2.

By means of this bite plate and a so-called articulator, a wax model is then prepared, this forming a provisional model for the abovementioned superstructure. This wax model comprises a relatively rigid bearing structure on which artificial teeth are fixed with wax. This provisional model likewise has hollows that correspond to the position of the abovementioned screws 2, in such a way that it can be positioned virtually perfectly in the oral cavity of the patient.

In a variant of the method according to the invention, the abovementioned hollows are not provided in this provisional model, but said hollows are formed during the fitting of the model, through depressions being formed in its bearing structure by the abovementioned screws 2.

After the provisional model has been placed on the corresponding jaw 1 of the patient in this way, a three-dimensional image is made of said jaw 1, together with this model and the abovementioned screws 2.

In order to obtain such a three-dimensional image, it is preferable to perform a so-called CT scan. The information from this three-dimensional image is preferably processed electronically, in order to make it possible to display it in a simple manner on, for example, a computer screen and to enable it to be used for certain so-called rapid prototyping techniques.

From this three-dimensional image, anatomical structures such as the shape of the bone and the position of the nerve bundles and the blood vessels in the jaw 1 are deduced. It is then determined at what positions in the lower jaw and according to what orientations implants can be placed in the jaw 1 without touching nerve bundles, blood vessels or other critical anatomical structures.

Figure 2:
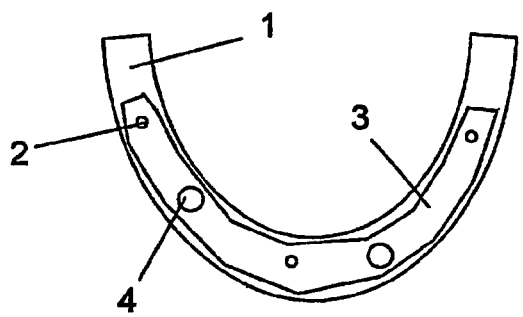
FIG. 2 is a diagrammatic top view of a part of a lower jaw with an aligning plate according to the invention.
Figure 3:
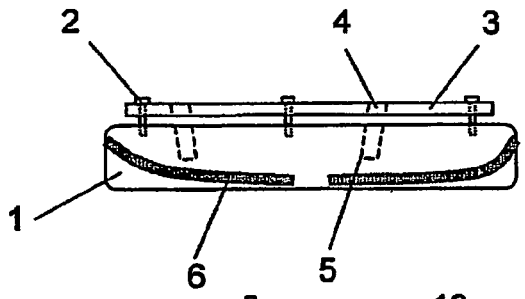
FIG. 3 is a diagrammatic front view of the lower jaw and the aligning plate of FIG. 2.

On the basis of this information, an aligning plate 3 is produced, having apertures 4 with a suitable orientation and diameter to allow said holes to be drilled through them in the bone of the jaw 1, in order to fit the abovementioned implants. For this purpose, the aligning plate 3 is placed on the jaw 1 in the manner shown in FIGS. 2 and 3. In addition to these apertures 4, means are also provided for fixing the. aligning plate 3 on the abovementioned screws 2. Said means more specifically comprise openings, the position of which corresponds to that of the screws 2, and which can connect up in a virtually exact fit with the latter.

In this way, the position of the abovementioned apertures 4 is determined relative to said screws 2, and the aligning plate 3 assumes a fixed position relative to the jaw 1 and the screws 2. This makes it possible in a simple manner to make a hole 5 by means of a drill, in a manner known per se, for each implant that is to be placed.

For making the abovementioned holes 5 it is preferable to use several bushes with an axial cylindrical opening, in the case of which their external dimensions virtually correspond to those of the apertures 4, in such a way that said bushes can be placed in the latter in a virtually exact fit with them. The axial cylindrical opening of the various bushes is, however, different. When the holes 5 are being drilled in the jaw 1, more specifically, different drills with increasing diameters are used in succession. This means that at the start of drilling of a hole 5 a drill with a small diameter is used, in which case a first bush, with a cylindrical opening whose diameter corresponds to that of the drill, is placed in the abovementioned aperture 4 of the aligning plate 3, in order to guide the drill, so that a very accurate hole can be drilled. A number of successive holes are drilled in this way, in each case a drill with a larger diameter being used, and in each case a bush with corresponding dimensions being placed in the aperture 4, until the hole obtained in this way is large enough for the placing of an implant As stated above, the position and the orientation of the abovementioned apertures 4 are selected in such a way that the blood vessels or the nerve bundles 6 or other critical anatomical structures cannot be touched during drilling in the jaw 1.

According to an advantageous embodiment of the method according to the invention, the aligning plate is made by means of the abovementioned rapid prototyping techniques. Such techniques are, for example, stereolithography, selective laser sintering, fused deposition modelling, laminated object prototyping, three-dimensional printing, and so forth. In a very interesting rapid prototyping technique the abovementioned aligning plate 3 is produced on the basis of the information from the abovementioned three-dimensional image by milling from, for example, a block of metal or plastic.

In addition to the abovementioned aligning plate 3, the superstructure is also made using one of these rapid prototyping techniques, starting, on the one hand, from the abovementioned provisional model and the abovementioned hollows that correspond to the position of the abovementioned screws 2, and, on the other hand, from the relative position of the abovementioned apertures 4 in the aligning plate 3, or therefore the desired position of the implants relative to the screws 2.

Through the use of the abovementioned screws 2 as reference elements, it is consequently no longer necessary to make an impression of the jaw 1 of a patient after the placing of the implants, and the superstructure can be produced immediately on the basis of the information from the abovementioned three-dimensional image.

The superstructure is preferably produced by means of a similar rapid prototyping technique to that used for making up the aligning plate 3.

In order to fix the abovementioned artificial teeth in a correct position on the superstructure 7, the abovementioned provisional model is placed on a holder, with the abovementioned hollows connecting up in a virtually exact fit with supporting points provided on said holder. The mutual position of said supporting points therefore corresponds to the mutual position of the abovementioned reference elements. The provisional model with the artificial teeth is then cast in a plastic, in order to form a so-called plastic key, said plastic key forming a contact face with the holder. The wax and the bearing structure are then removed from the plastic key according to techniques that are known per se, the artificial teeth remaining behind in a fixed position in the plastic. If a setting silicone is used for the abovementioned plastic, said plastic key is called a silicone key.

Finally, in order to fix the artificial teeth on the superstructure, the latter is placed on the holder, in which case the hollows corresponding to the reference elements connect up in a virtually exact fit with the abovementioned supporting points. In this way the superstructure assumes the same position relative to the holder as the provisional model during the making up of the plastic key. The plastic key is then placed over the superstructure, care being taken to ensure that the plastic key is positioned in an identical manner relative to the holder. This is carried out more specifically by placing the plastic key with the same contact surface and in the same way against the holder as was the case during its manufacture. Finally, a synthetic resin is placed in the plastic key, in a manner known per se, between the superstructure 7 and the artificial teeth. When this synthetic resin has set, in such a way that the teeth are immovably connected to the superstructure, the plastic key is removed from the superstructure and the artificial teeth.

Figure 4:
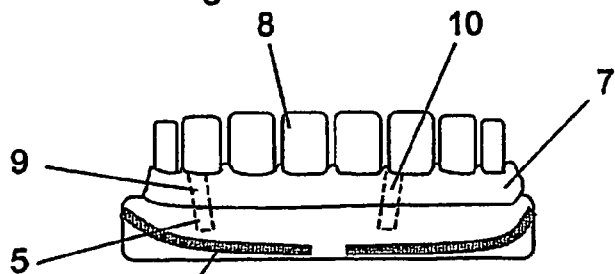
FIG. 4 is a diagrammatic front view of a part of a lower jaw with a superstructure provided with teeth according to the invention.

FIG. 4 shows diagrammatically a superstructure 7 produced in this way, with artificial teeth 8 placed on it. Said superstructure 7 is fitted on implants 9 and 10, which are provided in the holes 5 drilled in the lower jaw 1.

Figure 5:
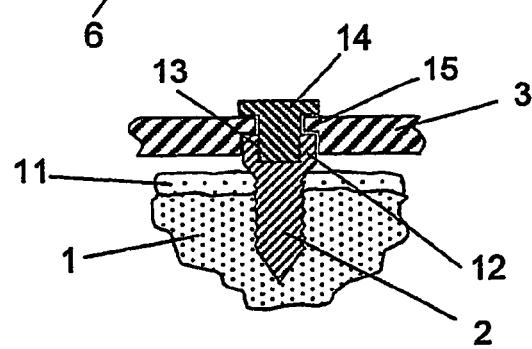
FIG. 5 is a diagrammatic cross section of a reference element together with an aligning plate, according to the invention.

FIG. 5 shows diagrammatically a reference element that is formed by a screw 2. Said screw 2 is fixed through the gum 11 in the bone of a jaw 1 and has a preferably polygonal head 12, which extends above the gum 11. The head 12 has on its top side a cylindrical threaded opening 13 which is coaxial with the screw 2. Fixed in this opening 13 is a bolt 14, which allows the abovementioned aligning plate 3 to be fixed to the screw 2.

For this purpose, the aligning plate 3 has at a position corresponding to that of the screw 2 an opening that connects up in a virtually exact fit with the head 12 of the screw 2, said opening having a collar 15 that rests on the top of the head 12. The abovementioned bolt 14 extends through the opening in the aligning plate 3.

In a variant of the above embodiment of the method and the aligning plate according to the invention, the abovementioned aligning plate 3 is formed by the superstructure 7, so that it is not necessary to manufactured a separate aligning plate 3. In such a case the abovementioned apertures 4 are made in the superstructure 7, and after the implants 9 and 10 have been placed the superstructure is fixed on said implants by means of screws or bolts suitable for the purpose.

The reference elements 2 are preferably removed from the jaw 1 before the final placing of the superstructure 7.

When reference is made in this description to the bone of a lower or an upper jaw (1), this also includes the bone parts connected to said jaw (1).

Notwithstanding the fact that in the above description and in the appended figures a superstructure that is fixed to a lower jaw with the aid of two implants has been described, the invention also relates to a method and an aligning plate in the case of which three or more implants are provided in the lower jaw, or in the case of which only one implant is used. In addition, the dental prosthesis produced in this way need not extend over the entire jaw 1, but it may have only a few teeth and be fitted on one implant. The invention is also equally usable for producing and fitting a superstructure for an upper jaw.

The invention is in no way limited to the embodiments of the method, the superstructure and the aligning plate according to the invention described above and proposed in the figures, but a number of variants can be considered within the scope of this invention, both as regards the reference elements and as regards the dimensions and shapes of the aligning plate.

The invention claimed is:

1. Method for producing a superstructure (7) provided with artificial teeth (8), which superstructure is fitted on at least one implant (9,10), which implant is provided in the oral cavity of a person and is adapted to be fixed in the bone of a lower or an upper jaw (1), and for producing an aligning plate (3) with at least one aperture (4) serving as a guide for drilling a hole (5) in the bone through the aperture (4) in the aligning plate, in which hole (5) said implant (9,10) is fixed, comprising the steps of:

fixing at least one reference element (2) in the bone, locating anatomical structures of the jaw (1) relative to said reference element (2), providing fixing means on said aligning plate (3) to fix the aligning plate (2) relative to said reference element (2), having fixed the reference element in the bone and located the anatomical structures relative to said reference element (2), selecting a position for the aperture (4) in the aligning plate (3) relative to said fixing means by taking into account the location of the anatomical structures so that critical anatomical structures, including nerve bundles, are not touched during the drilling of the hole (5) when the aligning plate (3) is fixed to the reference element (2) provided in said jaw (1) and providing said aperture (4) in the aligning plate (3) according to the selected position for the aperture (4).

2. The method according to claim 1, wherein a screw (2) is fixed in the bone to serve as the reference element.

3. The method according to claim 1, further providing means on the aligning plate (3) to detachably fix the aligning plate (3) on the reference element (2) before the hole (5) is drilled in the bone.

4. The method according to claim 3, wherein the means are formed by providing an opening in the aligning plate (3), which can connect up in a substantially exact fit with the reference element (2).

5. The method according to claim 1, further making an impression of the abovementioned jaw (1) with the reference element (2), and a provisional model of the superstructure (7) based on said impression, and thereafter making a three-dimensional image of the jaw (1) together with the provisional model and the reference element (2).

6. The method according to claim 5, wherein the three-dimensional image is obtained by carrying out a CT scan.

7. The method according to claim 5, wherein the aligning plate (3) is produced based on the three-dimensional image.

8. The method according to claim 5, wherein the three-dimensional image is processed electronically to produce the aligning plate (3) and/or the superstructure (7) by means of a rapid prototyping technique.

9. The method according to claim 1, wherein the aligning plate (3) is fixed to the reference element (2), the hole (5) is drilled, and the implant (9,10) is fixed in said hole (5), and then after the reference element (2) has been removed, the superstructure (7) is fitted on said implant (9,10).

10. The method according to claim 1, wherein a three-dimensional image is made of said jaw (1) together with said reference element (2), whereby said aligning plate (3) is produced based on the three-dimensional image by a rapid prototyping technique.

11. Method for producing an aligning plate (3) with at least one aperture (4) serving as a guide for drilling a hole (5) in the bone of a lower or an upper jaw (1) through said aperture (4) for fixing an implant (9,10) in the bone, comprising the steps of:
 fixing at least one reference element (2) in the bone,
 locating anatomical structures of the jaw (1) relative to said reference element (2),
 providing fixing means on said aligning plate (3) to fix the aligning plate (2) relative to said reference element (2),
 having fixed the reference element in the bone and located the anatomical structures relative to said reference element (2), selecting a position for the aperture (4) in the aligning plate (3) relative to said fixing means by taking into account the location of the anatomical structures so that critical anatomical structures, including nerve bundles, are not touched during the drilling of the hole (5) when the aligning plate (3) is fixed to the reference element (2) provided in the jaw (1) and providing said aperture (4) in the aligning plate (3) according to the selected position for the aperture (4).

12. The method according to claim 11, wherein a screw (2) is fixed in the bone to serve as the reference element.

13. The method according to claim 11, wherein the fixing means are formed by providing an opening in the aligning plate (3), which can connect up in a substantially exact fit with the reference element (2).

14. The method according to claim 11, further making an impression of the abovementioned jaw (1) with the reference element (2), and a provisional model of a superstructure (7) based on said impression, and thereafter making a three-dimensional image of the jaw (1) together with the provisional model and the reference element (2).

15. Method according to claim 14, wherein the three-dimensional image is processed electronically to produce the aligning plate (3) and/or the superstructure (7) by means of a rapid prototyping technique.

16. The method according to claim 11, wherein the aligning plate (3) is fixed to the reference element (2), the hole (5) is drilled, and the implant (9,10) is fixed in said hole (5), and then after the reference element (2) has been removed, a superstructure (7) is fitted on said implant (9,10).

17. Method for fixing at least one implant into the bone of a lower or an upper jaw by means of an aligning plate (3) having at least one aperture (4) serving as a guide for drilling a hole (5) in the bone through said aperture, in which said implant (9,10) is fixed, comprising the steps of:
 fixing at least one reference element (2) in the bone,
 locating anatomical structures of the jaw (1) relative to said reference element (2),
 providing fixing means on said aligning plate (3) to fix the aligning plate (2) relative to said reference element (2),
 having fixed the reference element in the bone and located the anatomical structures relative to said reference element (2), selecting a position for the aperture (4) in the aligning plate (3) relative to said fixing means by taking into account the location of the anatomical structures so that critical anatomical structures, including nerve bundles, are not touched during the drilling of the hole (5) when the aligning plate (3) is fixed to the reference element (2) provided in the jaw (1),
 providing said aperture (4) in the aligning plate (3) according to the selected position for the aperture (4),
 fixing said aligning plate (3) to the reference element (2) by means of said fixing means and, successively, guiding a drill through said aperture and drilling a hole (5) in the bone of the jaw (1),
 fixing said implant into said hole (5).

* * * * *